United States Patent [19]

Kollar

[11] 4,412,085
[45] Oct. 25, 1983

[54] PROCESS FOR PRODUCING ETHYLENE GLYCOL

[76] Inventor: John Kollar, 6 Spencer Ct., Wyckoff, N.J. 07481

[21] Appl. No.: 352,920

[22] Filed: Feb. 26, 1982

Related U.S. Application Data

[63] Continuation-in-part of Ser. No. 183,537, Sep. 2, 1980, Pat. No. 4,337,371, and a continuation-in-part of Ser. No. 286,721, Jul. 28, 1981, abandoned.

[51] Int. Cl.³ .................... C07C 31/20; C07C 29/00
[52] U.S. Cl. .................................................. 568/852
[58] Field of Search ........................................ 568/852

[56] References Cited
U.S. PATENT DOCUMENTS
4,337,371  6/1982  Kollar ............................... 568/852

OTHER PUBLICATIONS
Oyama, "J. Org. Chem.", Jul. 30, 1965, pp. 2429–2432.
The Merck Index, 6th Ed., 1952, p. 441.

Primary Examiner—J. E. Evans

[57] ABSTRACT

Ethylene glycol is prepared by reacting methanol, formaldehyde and from greater than 6 to about 25 weight percent of an organic peroxide in the presence of about 0.5 to about 35 weight percent of water based on the feed composition, the amount of water within said range being correlated with the peroxide content. The organic peroxide has the formula R—O—O—R¹ wherein R and R¹ are each an alkyl or aralkyl group having 3 to 12 carbon atoms.

9 Claims, 1 Drawing Figure

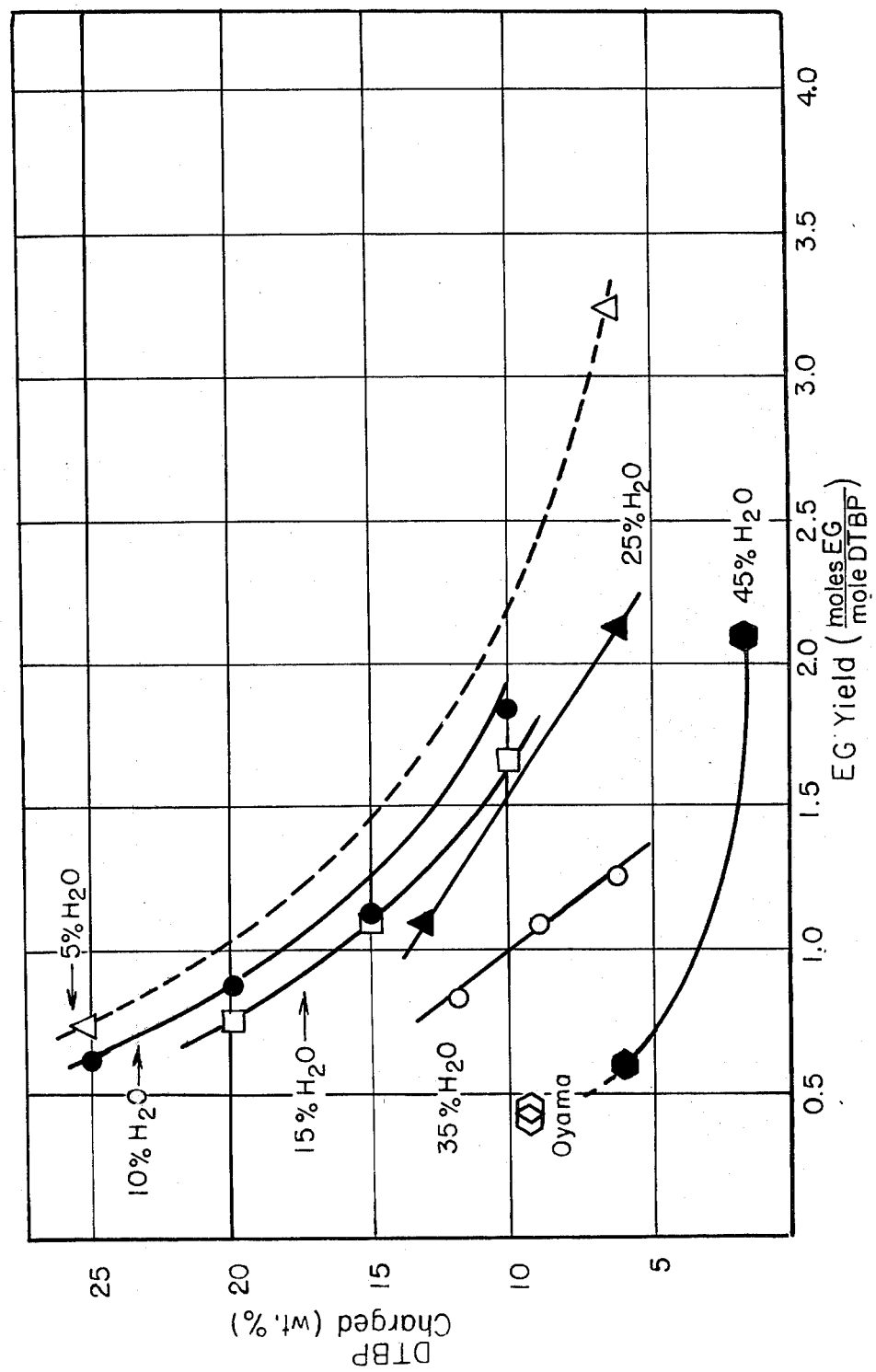

PROCESS FOR PRODUCING ETHYLENE GLYCOL

This application is a continuation-in-part application of U.S. Ser. No. 183,537 filed Sept. 2, 1980, entitled "Production of Ethylene Glycol by Reaction of Methanol, an Organic Peroxide and Formaldehyde," now U.S. Pat. No. 4,337,371, and also a continuation-in-part application of U.S. Ser. No. 286,721 filed July 28, 1981, entitled "Process for Producing Ethylene Glycol," now abandoned, the disclosures which are incorporated herein by reference.

This invention relates to a process for producing ethylene glycol from methanol.

BACKGROUND OF THE INVENTION

Dwindling petroleum reserves and increasing prices have placed an increased emphasis on the use of synthesis gas in place of oil as a starting material for producing various chemicals, such as methanol, formaldehyde and ethylene glycol. The advantage of synthesis gas is that it can be produced from raw materials other than petroleum, such as natural gas or coal, and potentially from oil shale and tar sands.

An example of an industrial process for the production of ethylene glycol utilizing synthesis gas as a starting material is the reaction of formaldehyde with carbon monoxide and water at high pressures (over 300 atmospheres) in the presence of an acid catalyst to produce hydroxyacetic (glycolic) acid, which is then reacted with methanol to give the methyl ester; the latter is then converted to the glycol by catalytic hydrogenation. See U.S. Pat. Nos. 2,316,564, issued Apr. 13, 1943 to Cockerill; 2,153,064, issued Apr. 4, 1939 to Larson; and 2,152,852; 2,385,448 and 2,331,094, issued Apr. 4, 1939, June 9, 1942 and Oct. 5, 1943, respectively, to Loder.

Another proposed process utilizing synthesis gas for the production of ethylene glycol is the reaction of methanol and carbon monoxide using a rhodium-catalyzed, high pressure process; see U.S. Pat. Nos. 4,115,428, issued to Vidal et al, and 4,115,433, issued to Cosby et al on Sept. 19, 1978.

With respect to the type of process for the production of ethylene glycol disclosed and claimed herein, it should be noted that the oxidative dimerization or dehydrodimerization of a large variety of organic compounds by peroxides is very old art that was pioneered by the preeminent free radical theoretician M. S. Kharasch and his students. These studies became the foundations of much subsequent free radical chemistry. Kharasch et al in *JACS* 65, 15, 1943 show the dehydrodimerization of acetic acid to succinic acid with acetyl peroxide in a 50 mole percent utilization selectivity based on acetyl peroxide, utilization selectivity being defined as the moles of dehydrodimer product made divided by the moles of peroxide converted. Isobutyric acid produced tetramethylsuccinic acid in a 42.4 mole percent utilization selectivity. Kharasch et al in *J. Org. Chem.* 10, 386, 1945 show the ester methyl chloroacetate being dimerized to dimethyldichloro succinate by acetyl peroxide in a 41 percent utilization selectivity. Kharasch et al in *J. Org. Chem.* 10, 401, 1945 show the dimerization of cumene and ethylbenzene with acetyl peroxide in 61.9 mole percent and 32.1 mole percent respectively to their dehydrodimers. Wiles et al in *I, E & C,* August 1949, page 1682, tell of the efficacy of di-t-butyl peroxide and 2,2bis(t-butylperoxy)butane for the dimerization of cumene to 1,1,2,2-tetramethyl 1,2-diphenylethane. The benzoate ester of benzyl alcohol was dimerized to the dibenzoate ester of the corresponding glycol, 1,2-diphenylene ethylene glycol, with di-t-butyl peroxide by Rust et al, *JACS* 70, 3258 (1948).

The literature is replete with many other examples showing production of dehydrodimers at very low concentrations at utilization selectivities of generally from 20–50 mole percent, based on the peroxide consumed. Such selectivities are generally too low for a process to be considered for commercial development.

In connection with ethylene glycol, two teachings involving peroxide-induced reactions should be mentioned:

The first is found in Schwetlick et al, *Angew. Chem.* 72, 1960, No. 21, pages 779 and 780, and involves heating a mixture of di-tertiary-butyl peroxide and methanol in a molar ratio of 1:20 in an autoclave and/or under reflux for a period of 10 hours at 140° C. A 26 percent yield of ethylene glycol is reported, with the statement being made that an increase in the alcohol excess raises the yields.

The second and more important of such other reaction paths to ethylene glycol, in terms of its relevance to the present invention, is described by Oyama in *J. Org. Chem.* 30, July, 1965, pages 2429–2432. In particular, Oyama shows the reaction of 9 moles of methanol, 1.8 moles of 15 percent aqueous formaldehyde and 0.45 moles of t-butyl peroxide (di-tertiary-butyl peroxide) at 140° C. for 12 hours to give 0.21 moles of ethylene glycol (Table I at the top of the right hand column on page 2430), with the statement being made immediately below Table I: "The yield of ethylene glycol in the reaction of formaldehyde with methanol is higher than that of t-butyl peroxide induced dimerization of methanol. This fact suggests that hydroxymethyl radical (D) adds to formaldehyde." Oyama describes in greater detail how this reaction was run and the products obtained, and contrasts it with the dehydrodimerization of methanol in the presence of t-butyl peroxide and the absence of formaldehyde, in the "Experimental" section beginning at page 2431 (particularly the sections headed "Reaction of Methanol with Formaldehyde" and "Dimerization of Methanol" on page 2432).

The yields of ethylene glycol obtained by Oyama are fairly low. Oyama's only run with methanol—that involving the above-described reaction of methanol, aqueous formaldehyde and t-butyl peroxide at 140° C. for 12 hours—gave only 1.86 weight percent of ethylene glycol.

The above-described reaction can be made to produce higher yields of ethylene glycol by substantially decreasing the amount of organic peroxide employed, relative to the amounts of formaldehyde and methanol present, from that employed by Oyama. Moreover, increasing the amount of methanol and decreasing the amount of water, relative to the other components of the reaction mixture, in contrast to the amounts employed by Oyama, also appear to contribute to the production of higher yields of ethylene glycol. Thus, for example, heating a mixture of 78.5 weight percent of methanol, 1.5 weight percent of di-tertiary-butyl peroxide, 6.9 weight percent of formaldehyde and 13.1 weight percent of water at 155° C. for 2 hours gave a yield of 4.5 weight percent of ethylene glycol in the product mixture. This is equivalent to a yield of about 7.1 moles of ethylene glycol per moel of di-tertiarybutyl peroxide employed. (Oyama obtained 0.466 mole of ethylene glycol per mole of di-tertiary-butyl peroxide in his reaction). This improvement in which the amount of peroxide employed is up to 6% by weight of the reaction mixture, is more fully disclosed in the copending parent of this application, U.S. Ser. No. 183,537, filed Sept. 2, 1980.

Another copending parent application, U.S. Ser. No. 286,721 filed July 28, 1981, describes the production of ethylene glycol from methanol and an organic peroxide, alone or in the presence of formaldehyde and water reacted in the presence of a basic material in an amount sufficient to reduce the hydrogen ions that are being formed in the reaction without unduly reducing ethylene glycol production due to by-product formation. In this application, the basic material in the reaction reduced the acids, such as formic acid, are formed in the reaction which catalyze the formation of methylal from methanol and formaldehyde. Keeping the formation of methylal to minimum is highly desirable in order to avoid unduly large or expensive distillation requirements necessary for the purification of the ethylene glycol product.

THE INVENTION

In accordance with the process of this invention, ethylene glycol is produced by reacting methanol, an organic peroxide in an amount of from greater than 6 to about 25 weight percent, formaldehyde and water in an amount of from about 0.5 to about 35 weight percent based on the weight of the weight of the reaction mixture. The amount of water used is dependent on the amount of peroxide used to achieve the desired result. The amount of ethylene glycol produced by this process is larger than that produced by the process described in the Oyama reference discussed earlier which employs 40.5% methanol, 7.55% formaldehyde, 9.18% di-tertiary-butyl peroxide and 42.77% water based on the weight of the reaction mixture. It has been discovered in this invention that if the water content of the reaction is reduced to below 35%, improvements in amounts of ethylene glycol to di-tertiary-butyl peroxide (mole ratio basis) are achieved over that of the Oyama reference using peroxide amounts greater than 6 to about 25 percent. In addition to the ethylene glycol improvement, higher amounts of tertiary-butyl alcohol to di-tertiary-butyl peroxide (mole ratio basis) are achieved in the process of this invention compared to the Oyama reference. The mole ratio of acetone to di-tertiary-butyl peroxide was generally higher in the Oyama reference than the acetone/di-tertiary-butyl peroxide ratio of the present invention. Tertiary-butyl alcohol production is of particular significance in its use as an intermediate for gasoline additives as well as a gasoline additive itself.

For purposes of this invention, the amounts of organic peroxide and water used range as follows:

| Peroxide | Water |
|---|---|
| greater than 6 to about 12 weight percent | about 0.5 to about 35 weight percent |
| greater than about 12 to about 15 weight percent | about 0.5 to about 25 weight percent |
| greater than about 15 to about 20 weight percent | about 0.5 to about 15 weight percent |
| greater than about 20 to about 25 weight percent | about 0.5 to about 10 weight percent |

The amount of formaldehyde contained in the reaction mixture is from about 0.5 to about 13 weight percent, preferably from about 2 to about 12 weight percent. The amount of methanol present in the reaction mixture is the remaining amount of reaction product to add up to 100%. For example, the following ranges of amounts of reactants can be used:

| Peroxide Wt % | Water Wt % | Formaldehyde Wt % | Methanol Wt % |
|---|---|---|---|
| greater than 6 to 12 | 0.5–35 | 2–12 | 41–91.5 |
| greater than 12 to 15 | 0.5–25 | 2–12 | 48–85.5 |
| greater than 15 to 20 | 0.5–15 | 2–12 | 53–82.5 |
| greater than 20 to 25 | 0.5–10 | 2–12 | 53–77.5 |
| A preferred range is: | | | |
| greater than 6 to about 10 | 5–10 | 2–12 | 68–87 |

This reaction will generally be carried out at a temperature of from about 100° C. to about 200° C., preferably from about 125° C. to about 175° C., at a residence time of no higher than about 8 hours, usually from about 0.25 hour to about 8 hours, and preferably from about 0.5 to about 4 hours. Generally, the higher the temperature, the lower the reaction time necessary to bring the reaction to a desired state of completion. There is little or no criticality in the pressure at which the reaction is carried out. Pressures of between autogenous pressure to about 600 psig can be utilized.

The organic peroxide employed in the process of this invention has the formula

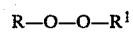

$$R-O-O-R^1$$

wherein R and $R^1$ are each an alkyl or aralkyl group having 3 to 12 carbon atoms. Organic peroxides which may be employed are, for example, di-tertiary-butyl peroxide, di-cumyl peroxide, tertiary-butyl cumyl peroxide and tertiary-butylethylbenzyl peroxide. The preferred organic peroxide is di-tertiary-butyl peroxide.

An inert solvent may be employed in the process, although in most cases it is preferred to operate without one. Any solvent which does not react under conditions of the process may be employed, e.g. benzene and tertiary-butyl alcohol. When a solvent is employed, it will generally be in an amount up to about 25 percent by weight of the total reaction medium, although larger amounts can be used in some instances.

The reactions may be carried out batchwise wherein a reactor such as stirred autoclave is charged with the initial reaction mixture which is then subjected to reaction, after which the entire reaction mixture is withdrawn and purified. Another batchwise processing technique is to charge the methanol, water and portions of the formaldehyde (usually mixed with some water) and peroxide as the initial reaction mixture and then adding the remaining portions of the formaldehyde and peroxide and in some cases basic material, which are sequentially and incrementally added to the methanol reaction medium. After all of the portions of reactants are added, the reaction is continued until the desired degree of reaction has taken place, after which the product mixture is withdrawn and purified. Another technique is a semi-continuous method in which the initial reaction mixture and incremental additions of reactants are charged to the methanol reaction medium, reaction takes place and the product mixture periodically withdrawn from the reactor and purified.

A continuous reaction can be carried out in a reactor constructed so that under the conditions of reaction, a glycol concentration gradient occurs between the point where the first portions of peroxide and formaldehyde are added and that at which the glycol-containing product is withdrawn. Thus, subsequent portions of peroxide and formaldehyde are added between these two points. For example, a continuous process may be carried out by causing the liquid reaction medium to flow through a pipe and adding portions of the formaldehyde and peroxide reactants at intervals along the pipe, forming a moving reaction medium containing a concentration gradient of glycol as it travels through the pipe. Thus, the individual portions of the reactants are added in a controlled manner along the pipe to the specific moving reaction medium until all the portions of the reactants have been added. At the end of the pipe reactor, the reaction of each portion of the reactants in the reaction medium has occurred at a conversion level to provide a product stream containing the desired amount of ethylene glycol. Alternatively, a baffled reactor may be employed containing a liquid reaction medium with a glycol concentration gradient between the point of entry of the initial feed stream and the point of exit of the product stream, wherein additional portions of peroxide and formaldehyde are added between the two points. In each case, the product mixture may then be purified using conventional techniques such as distillation or solvent extraction to obtain ethylene glycol in the desired product, preferably fiber grade, and by-products such as tertiary-butyl alcohol, methylal, methyl formate, glycerine and acetone.

The following examples will illustrate the invention.

EXAMPLES 1-18

An initial reaction mixture containing methanol (MeOH), di-tertiary-butyl peroxide (DtBP), formaldehyde ($CH_2O$) and water were charged to a stirred autoclave in the following manner: all but about 20 weight percent of the methanol in the initial charge, formaldehyde and water were added to a stirred autoclave at room temperature. The mixture was then heated up to reaction temperature and a solution of di-tertiary-butyl peroxide in the remaining 20 weight percent of methanol was added to the autoclave to initiate the reaction. A reaction pressure of 500 psig was maintained with nitrogen. After the prescribed reaction time, the product mixture was removed from the autoclave and analyzed for ethylene glycol (EG), acetone (A), tertiary-butyl alcohol (TBA), unreacted di-tertiary-butyl peroxide and other products present in minor amounts.

As a basis for comparison of this invention with the Oyama reference described previously, Example 15 illustrates the results of the Oyama process. This run was made by charging methanol, di-tertiary-butyl peroxide, formaldehyde and water to 304 stainless steel Hoke reactor at atmospheric pressure. The reactor was capped and placed in a thermostated oil bath held at the stated reaction temperature and allowed to react for 1 hour at autogenous pressure. After the reaction time was completed, the reactor was cooled by quenching, vented, discharged and analyzed for ethylene glycol, acetone, tertiary-butyl alcohol, unreacted di-tertiary-butyl peroxide and other products present in minor amounts.

Examples 16, 17 and 18 illustrate the use of water from 35.7 to 45 weight percent with peroxide, formaldehyde and methanol reacted in a 304 stainless steel Hoke reactor at atmospheric pressure. In each of these runs 0.015 weight percent sodium bicarbonate was added to the initial reaction mixture. The reactor was capped and placed in a thermostated oil bath held at 155° C. for 1 hour at autogenous pressure. After the reaction was completed, the reactor was cooled by quenching, vented, discharged and analyzed for ethylene glycol, acetone, tertiary-butyl alcohol, unreacted di-tertiary-butyl peroxide and other products present in minor amounts. In Example 16, the analysis of ehtylene glycol and unreacted di-tertiary-butyl peroxide were determined but acetone and tertiary-butyl alcohol were not determined.

The results of all of the above examples are shown in Table I which sets out the composition of the initial charge, temperature, pressure and reaction time employed for the reaction.

The results of Example 15 (the Oyama reference) for ethylene glycol production is similar to the results obtained in the reference. Comparing the results of Example 15 with Examples 1-14 which illustrate the results of the present invention, it should be noted that Examples 1-14 all produce higher mole ratios of ethylene glycol/di-tertiary-butyl peroxide and tertiary-butyl alcohol/di-tertiary butyl peroxide than does the Oyama reference run of Example 15. In regard to acetone, Example 15 produces a higher mole ratio of acetone/di-tertiary-butyl peroxide than the runs of Examples 1-14.

Examples 16 to 18 illustrate the use of over 35 weight percent of water in the reaction mixture which is outside the scope of this invention. Even though a base, i.e. 0.015 weight percent of sodium bicarbonate, was employed in the reaction mixture which, in accordance with the invention claimed in copending application Ser. No. 286,721 filed July 28, 1981, has the effect of reducing the formation of by-product methylal and raising the production of ethylene glycol, the weight percent of glycol produced in these examples was below that obtained by Oyama.

TABLE I

| Ethylene Glycol Production | | | | | | | | | | | | | |
|---|---|---|---|---|---|---|---|---|---|---|---|---|---|
| Examples | Initial Charge Wt % | | | | Temperature °C. | Reaction Time Hrs. | Pressure psig | Products Wt % | | | | Product Mole Ratios** | | |
|  | DtBP | $CH_2O$ | MeOH | $H_2O$ |  |  |  | EG | A | TBA | DtBP | EG/DtBP | A/DtBP | TBA/DtBP |
| 1 | 6 | 10 | 79 | 5 | 155 | 1 | 500 | 7.90 | 2.24 | 2.70 | 0.25 | 3.24 | 1.02 | 0.93 |
| 2 | 9 | 10 | 46 | 35 | 155 | 1 | 500 | 4.10 | 4.72 | 1.92 | 0.29 | 1.11 | 1.41 | 0.43 |
| 3 | 12 | 10 | 53 | 25 | 155 | 1 | 500 | 5.35 | 6.50 | 3.20 | 0.58 | 1.10 | 1.48 | 0.55 |
| 4 | 6 | 10 | 59 | 25 | 155 | 1 | 500 | 5.20 | 3.38 | 1.94 | 0.26 | 2.13 | 1.54 | 0.67 |
| 5 | 10 | 10 | 65 | 15 | 155 | 1 | 500 | 6.70 | 4.90 | 3.90 | 0.48 | 1.66 | 1.34 | 0.81 |
| 6 | 15 | 10 | 60 | 15 | 155 | 1 | 500 | 6.70 | 7.00 | 5.60 | 0.71 | 1.10 | 1.28 | 0.77 |
| 7 | 20 | 10 | 55 | 15 | 155 | 1 | 500 | 6.20 | 9.99 | 7.60 | 0.90 | 0.76 | 1.36 | 0.79 |

TABLE I-continued

Ethylene Glycol Production

| Examples | Initial Charge Wt % | | | | Temperature °C. | Reaction Time Hrs. | Pressure psig | Products Wt % | | | | Product Mole Ratios** | | |
|---|---|---|---|---|---|---|---|---|---|---|---|---|---|---|
| | DtBP | CH$_2$O | MeOH | H$_2$O | | | | EG | A | TBA | DtBP | EG/DtBP | A/DtBP | TBA/DtBP |
| 8 | 20 | 10 | 60 | 10 | 155 | 1 | 500 | 7.00 | 8.80 | 7.90 | 0.98 | 0.88 | 1.21 | 0.82 |
| 9 | 15 | 10 | 65 | 10 | 155 | 1 | 500 | 7.00 | 7.35 | 6.60 | 0.59 | 1.14 | 1.33 | 0.90 |
| 10 | 10 | 10 | 70 | 10 | 155 | 1 | 500 | 7.38 | 4.20 | 4.19 | 0.58 | 1.84 | 1.16 | 0.88 |
| 11 | 12 | 10 | 43 | 35 | 155 | 1 | 500 | 3.93 | 6.43 | 2.41 | 0.67 | 0.82 | 1.48 | 0.42 |
| 12 | 25 | 10 | 55 | 10 | 155 | 1 | 500 | 6.05 | 10.8 | 10.5 | 1.50 | 0.61 | 1.20 | 0.88 |
| 13 | 25 | 10 | 62.7 | 2.3 | 155 | 1 | 500 | 7.36 | 9.73 | 11.7 | 2.10 | 0.76 | 1.11 | 1.01 |
| 14 | 25 | 10 | 60 | 5 | 155 | 1 | 500 | 6.89 | 10.5 | 11.1 | 2.70 | 0.73 | 1.23 | 0.98 |
| 15 | 9.3 | 7.6 | 41.1 | 42.0 | 155 | 1 | Autogenous | 1.59 | 5.50 | 1.73 | 0.03 | 0.40 | 1.55 | 0.37 |
| 16* | 6.1 | 10.2 | 46 | 35.7 | 155 | 1 | Autogenous | 3.20 | — | — | 0.13 | 1.26 | — | — |
| 17* | 1.5 | 10.0 | 43.5 | 45 | 155 | 1 | Autogenous | 1.31 | 1.04 | 0.38 | 0.03 | 2.10 | 1.84 | 0.51 |
| 18* | 6.0 | 6.0 | 43 | 45 | 155 | 1 | Autogenous | 1.51 | 3.20 | 1.61 | 0.02 | 0.59 | 1.40 | 0.53 |

*0.015 weight percent sodium bicarbonate added
**Based on di-tertiary-butyl peroxide consumed The results of Examples 1–18, illustrating a correlation of di-tertiary-butyl peroxide charged (weight percent) to the mole ratio of ethylene glycol/di-tertiary-butyl peroxide obtained at various levels of water, are plotted on the graph shown in the drawing. Example 13 is the only example not plotted on the graph since only one point of a 2.3 weight percent water run is available. The graph illustrates that as the amount of water is decreased, higher amounts of di-tertiary-butyl peroxide can be used to achieve better results than those of the Oyama reference. Thus the range of proportion of peroxide which may be used corresponding to certain ranges of water content are as follows:

| Peroxide | Water |
|---|---|
| greater than 6 to about 12 weight percent | about 0.5 to about 35 weight percent |
| greater than about 12 to about 15 weight percent | about 0.5 to about 25 weight percent |
| greater than about 15 to about 20 weight percent | about 0.5 to about 15 weight percent |
| greater than about 20 to about 25 weight percent | about 0.5 to about 10 weight percent |

EXAMPLES 19–22

These examples illustrate the use of equivalent total amounts of reactants used in a single stage reaction and multiple stage reactions to produce ethylene glycol (EG) by the reaction of formaldehyde (CH$_2$O) containing water (H$_2$O), di-tertiary-butyl peroxide (DtBP) and methanol (MeOH) in the presence of sodium bicarbonate (NaHCO$_3$). The formaldehyde used in these examples contained 4.54 parts per million sodium hydroxide per one weight percent formaldehyde used. The reactor was a 316 stainless steel 1″ diameter pipe having a capacity of approximately 85 millimeters liquid. In a one stage reaction, all the reacting ingredients were placed in the reactor which was sealed and heated to 155° C. for 1 hours at autogenous pressure. In a staged reaction, a portion of the reactants of di-tertiary-butyl peroxide, formaldehyde and water and sodium bicarbonate were initially added to the reactor containing all the methanol heated to 155° C. for one hour. After the first hour of reaction, additional portions of the reactants were added and the reaction was conducted for another hour. After the second hour, the remainder of the reactants were added to the reactor and the reaction conducted for the final hour. After the reaction was completed in the first stage or in each multiple stage reaction, the reactor was cooled by quenching, vented, discharged and the contents analyzed by gas chromatography for ethylene glycol (EG) and other products.

The results of these examples are shown in Table II which sets out the composition of total amounts of peroxide, formaldehyde and water charged to the reactor containing the methanol in the various stages. The amounts of reactants used are reported as weight percent of the total material in the reactor up to that stage. The amounts of ethylene glycol are reported as weight percent of the total product mixture.

TABLE II

| Examples | Type of Reaction | | Reactants Added | | | NaHCO$_3$ Parts Per Million | Reaction Temp °C. | Reaction Time Hrs. | Ethylene Glycol Wt % |
|---|---|---|---|---|---|---|---|---|---|
| | | | DtBP Wt % | H$_2$CO Wt % | H$_2$O Wt % | | | | |
| 19 | 1 stage | | 7.0 | 14.0 | 1.91 | 100 | 155 | 1 | 8.75 |
| 20 | 3 stage | 1st stage | 3.0 | 6.0 | .8 | 50 | 155 | 1 | 6.14 |
| | | 2nd stage (total) | 5.0 | 10.0 | 1.36 | 75 | 155 | 1 + 1 = 2 | 9.28 |
| | | 3rd stage (total) | 7.0 | 14.0 | 1.91 | 100 | 155 | 2 + 1 = 3 | 11.68 |
| 21 | 1 stage | | 6.42 | 11.77 | 1.60 | 100 | 155 | 1 | 8.92 |
| 22 | 3 stage | 1st stage | 3.0 | 7.0 | 0.95 | 50 | 155 | 1 | 7.32 |
| | | 2nd stage (total) | 4.77 | 9.48 | 1.33 | 75 | 155 | 1 + 1 = 2 | 9.58 |
| | | 3rd stage (total) | 6.42 | 11.77 | 1.60 | 100 | 155 | 2 + 1 = 3 | 11.48 |

What is claimed is:

1. In a process for producing ethylene glycol by reacting methanol, an organic peroxide, and formaldehyde in the presene of water, said organic peroxide having the formula R—O—O—R$^1$ wherein R and R$^1$ each is an alkyl or aralkyl group containing 3 to 12 carbon atoms, the improvement comprising utilizing organic peroxide and water in the following ranges:

| Peroxide | Water |
|---|---|
| greater than 6 to about 12 weight percent | about 0.5 to about 35 weight percent |
| greater than about 12 to about 15 weight percent | about 0.5 to about 25 weight percent |
| greater than about 15 to about 20 weight percent | about 0.5 to about 15 weight percent |
| greater than about 20 to about 25 weight percent | about 0.5 to about 10 weight percent | the above amounts based on the total weight of methanol, organic peroxide, formaldehyde and water present in the initial reaction mixture, the amount of formaldehyde present being from about 0.5 to about 13 weight percent.

2. The process of claim 1 wherein the organic peroxide is di-tertiary-butyl peroxide.

3. The process of claim 1 wherein the reaction time is no greater than 8 hours.

4. The process of claim 2 wherein the remainder of the initial reaction mixture is methanol and the reaction temperature is from about 100° to about 200° C. and the reaction time is from about 0.25 to about 8 hours.

5. The process of claim 2 wherein the initial reaction mixture contains from about 41 to about 91.5 weight percent of methanol, from greater than 6 to about 12 weight percent of di-tertiary-butyl peroxide, from about 0.5 to about 35 weight percent water and from about 2 to about 12 weight percent formaldehyde, the reaction temperature is from about 125° C. to about 175° C. and the reaction time is from about 0.5 to about 4 hours.

6. The process of claim 2 wherein the initial reaction mixture contains about 48 to about 85.5 weight percent of methanol, from about 12 to about 15 weight percent of di-tertiary-butyl peroxide, from about 0.5 to about 25 weight percent of water and from about 2 to about 12 weight percent formaldehyde, the reaction temperature is from 125° C. to about 175° C. and the reaction time is from about 0.5 to about 4 hours.

7. The process of claim 2 wherein the initial reaction mixture contains about 53 to about 82.5 weight percent of methanol, from about 15 to about 20 weight percent of di-tertiary-butyl peroxide, from about 0.5 to about 15 weight percent water and from about 2 to about 12 weight percent formaldehyde, the reaction temperature is from 125° C. to about 175° C. and the reaction time is from about 0.5 to about 4 hours.

8. The process of claim 2 wherein the initial reaction mixture contains about 53 to about 77.5 weight percent of methanol, about 20 to about 25 weight percent of di-tertiary-butyl peroxide, about 0.5 to about 10 weight percent water and about 2 to about 12 weight percent formaldehyde, the reaction temperature is from 125° C. to about 175° C. and the reaction time is from about 0.5 to about 4 hours.

9. The process of claim 2 wherein the initial reaction mixture contains from about 68 to about 87 weight percent methanol, from greater than 6 to about 10 weight percent of di-tertiary-butyl peroxide, from about 2 to about 12 weight percent formaldehyde and from about 5 to about 10 weight percent water, the reaction temperature is from 125° C. to about 175° C. and reaction time is from about 0.5 to about 4 hours.

* * * * *